United States Patent
Heikkilä et al.

(10) Patent No.: US 6,764,706 B1
(45) Date of Patent: Jul. 20, 2004

(54) PROCESS FOR THE CRYSTALLIZATION OF XYLITOL

(75) Inventors: Heikki Heikkilä, Espoo (FI); Johanna Nygren, Virkkala (FI); Marja-Leena Sarkki, Kantvik (FI); Håkan Gros, Kantvik (FI); Olli-Pekka Eroma, Kotka (FI); Julita Pearson, Kent (GB); Tammy Pepper, Surrey (GB)

(73) Assignee: Xyrofin OY (FI)

( * ) Notice: Subject to any disclaimer, the term of this patent is extended or adjusted under 35 U.S.C. 154(b) by 0 days.

(21) Appl. No.: 09/674,543

(22) PCT Filed: May 17, 1999

(86) PCT No.: PCT/FI99/00423

§ 371 (c)(1),
(2), (4) Date: Dec. 27, 2000

(87) PCT Pub. No.: WO99/59426

PCT Pub. Date: Nov. 25, 1999

(30) Foreign Application Priority Data

May 18, 1998 (FI) .................................................. 981104

(51) Int. Cl.$^7$ ............................................. A23L 1/236
(52) U.S. Cl. ........................ 426/548; 426/3; 426/467; 426/471; 426/474
(58) Field of Search ........................... 426/9, 548, 465, 426/467, 471, 474

(56) References Cited

U.S. PATENT DOCUMENTS

| | | | |
|---|---|---|---|
| 4,066,711 A | | 1/1978 | Melaja et al. |
| 4,105,801 A | * | 8/1978 | Dogliotti ............... 426/99 |
| 4,698,101 A | | 10/1987 | Koivurinta |
| 5,139,795 A | * | 8/1992 | DuRoss ............... 426/3 |
| 5,162,517 A | * | 11/1992 | Darsow ............... 536/124 |
| 5,204,115 A | | 4/1993 | Olinger et al. |

FOREIGN PATENT DOCUMENTS

| | | |
|---|---|---|
| DE | 44 39 828 A1 | 5/1996 |
| DK | 133603 | 6/1976 |
| EP | 0 305 356 A1 | 3/1989 |
| EP | 0 380 219 A2 | 8/1990 |
| EP | 0 387 950 A1 | 9/1990 |
| EP | 0 529 852 A1 | 3/1993 |
| FI | 942267 | 11/1994 |
| JP | 49[1974]-16929 | 8/1970 |
| WO | WO 92/10168 | 6/1992 |
| WO | WO 96/27029 | 9/1996 |

OTHER PUBLICATIONS

Bar, A., "Caries Prevention with Xylitol: A Review of the Scientific Evidence", *Wld. Rev. Nutr. Diet*, vol. 55: 183–209 (1988).

Tanzer, J., "Xylitol chewing gum and dental caries", *International Dental Journal*, vol. 45: 65–76 (1995).

Edgar, W.M., "Sugar substitutes, chewing gum and dental caries—a review", *British Dental Journal*, vol. 184(1) 29–32 (1998).

Kim, H.S., et al., "The Crystal Structure of Xylitol", *Acta Cryst.*, vol. B25: 2607–2613 (1969).

Nabors, L.O., et al., *Alternative Sweeteners, Second Ed.*, p. 349–352 (1991).

Carson, J. F., et al., "A New Form of Crystalline Xylitol", *J. Am. Chem. Soc.*, vol. 65: 1777–1778 (1993).

* cited by examiner

*Primary Examiner*—Leslie Wong
(74) *Attorney, Agent, or Firm*—Scully, Scott, Murphy & Presser (57) ABSTRACT

The invention relates to a novel process for the crystallization of xylitol by contacting a xylitol solution with particulate xylitol suspended in a gas, drying the material to produce a multitude of microrystals and conditioning the material into an agglomerated product. The invention also relates to a particulate crystalline xylitol product having novel properties, to the use thereof in confectionery, foodstuff pharmaceuticals and oral hygiene products, and to special products comprising the same.

26 Claims, 3 Drawing Sheets

PROCESS FOR THE CRYSTALLIZATION OF XYLITOL

The present invention relates to a novel process for the crystallization of xylitol, to a particulate crystalline xylitol product having novel properties, to the use thereof in confectionery, foodstuffs, pharmaceuticals and oral hygiene products, and to special products comprising the same. The present invention specifically provides a crystalline xylitol product, wherein the crystals are produced by microcrystallization of xylitol from a liquid solution of xylitol.

Xylitol is a naturally occurring five carbon sugar alcohol which has the same sweetness as sugar and a caloric content which is less than that of sugar. Xylitol is found in small amounts in many fruits and vegetables and is produced in the human body during normal metabolism. Xylitol is attractive as a sugar substitute in food contexts because of its known metabolic, dental and technical characteristics. Xylitol is metabolized largely independent of insulin, so it can be safely consumed by non-insulin dependent diabetics.

Xylitol is well established as a non-cariogenic substance, i.e. xylitol does not contribute to caries formation. Significant data also exists which supports the view that xylitol is not only non-cariogenic, but actively suppresses the formation of new caries and may even re-harder existing lesions by inducing remineralization, i.e. it is a cariostatic material.

A summary of clinical data regarding the effects of xylitol and its possible mechanisms is set forth in Bar, Albert, *Caries Prevention With Xylitol: A Review of a Scientific Evidence*, 55 Wld. Rev. Nutr. Diet. 183–209 (1983); Tanzer, Jason M., *Xylitol chewing gum and dental caries*. International Dental Journal (IDJ), Vol. 45, No. 1. (Suppl. 1), 65–76 (1995); Edgar, W. M., *Sugar substitutes, chewing gum and dental caries—a review*. British Dental Journal (BDJ), Vol. 184, No. 1, 29–32 (January 1998).

Xylitol has been widely used as a sweetening agent resembling sugar. For instance, xylitol may be used in confectionery, bakery products, cereals, desserts, jams, beverages, chocolate, chewing gums, ice-cream, and in various dietetic products. Xylitol has also been used in the production of oral hygiene products such as tooth pastes, and in the manufacture of pharmaceuticals.

Xylitol has been commercially produced in crystalline form, the crystallization being performed by conventional liquid crystallization techniques from an aqueous solution. The properties and production of xylitol has been described, for instance, in Carson, J. F. et al, J. Am. Chem. Soc. 65 (1993) p. 1777–1778; Kim, H. S. et al, Acta. Cryst. (1969), B25, 2607; Nabors, L. O. et al. Alternative Sweeteners, Second Ed., 1991, p. 349–352; as well as U.S. Pat. No. 4,066,711 and 4,698,101.

The crystallization of xylitol from a liquid such as from an aqueous or ethanolic solution requires specific crystallization conditions and fairly long crystallization times due to the nature of prior art crystallization methods, all of the xylitol in the solution cannot be obtained in crystalline form. A part of the xylitol will always remain in the mother liquor and will be discarded with the mother liquor even after repeated series of crystallizations. This provides a comparatively low yield of the process.

Xylitol has also been produced in solid form by granulation as described in U.S. Pat. No. 5,204,115. Granulation of xylitol with a binder such as polydextrose has been shown to improve the tabletting properties of xylitol. There is no disclosure of successful spray drying of xylitol alone.

In connection with spray drying of sorbitol, minor amounts of xylitol or other polyols have been added to the spray solution As described in DE Patent 44 39 858 (Merck Patent GmbH). According to the said Patent, 5% or 7.5% of xylitol, respectively, were added into an aqueous sorbitol solution and spray dried to provide a tablettable product. There is no indication that xylitol alone has been spray dried in the same manner.

Thus, there exists a need for improving the production of solid xylitol products and the present invention aims at satisfying that need.

The object of the present invention is thus, to provide a solid particulate crystalline xylitol product.

Another object of the present invention is to provide crystalline xylitol product in a process which transforms a xylitol liquid into a solid xylitol product in one single overall operation.

An object of the invention is also to provide a novel particulate xylitol product which is suitable for use in the food industry as well as in the pharmaceutical and oral hygiene product industry.

An object is also to provide novel edible, pharmaceutical and oral hygiene products containing xylitol.

Consequently, the present invention, which is defined in the appended claims, provides a novel process for producing crystalline xylitol. Said process comprises contacting a liquid containing dissolved xylitol with gas suspended solid particles containing microcrystalline xylitol; causing substantial removal of the solvent component of said liquid and allowing the resulting xylitol material to form an essentially solid composition of matter comprising a multitude of microcrystals of xylitol; and causing said xylitol composition to be conditioned during a further drying step to provide a product consisting essentially throughout its entire structure of a multitude of microcrystals of xylitol agglomerated together in a random manner.

In a preferred embodiment of the invention an aqueous solution of xylitol is brought into contact with fluidized particles of microcrystalline xylitol, the wetted particles are dried in a flow of hot gas, and the xylitol on the surface of the particles is allowed to form new microcrystals on said surface.

By further conditioning the particles, the microcrystallization is allowed to proceed for a sufficient time to provide a final product consisting essentially of microcrystalline xylitol.

In a preferred embodiment of the invention the wetted particles are substantially dried while falling down with a co-current air stream and allowed to settle into a porous layer of agglomerated microcrystallizing xylitol, which is then conditioned and cooled. The microcrystallization conditions are selected so that the cooled layer is dry, porous and brittle. If desired, the layer may be broken up into smaller fractions. Only a mild crushing action is needed to break up the agglomerated mass of microcrystals. The agglomerated product will primarily be broken up at the interfaces between individual crystals rather than by disrupting the crystals themselves.

In another embodiment of the invention the particles are retained in a suspended state in an air stream while additional liquid is sprayed onto their surfaces until the particles have grown to a predetermined size or weight. The particles are then removed from the air stream, e.g. by gravity and conditioned as described above.

The gas suspended microcrystalline xylitol particles are preferably provided by recirculating a portion of the microcrystalline xylitol produced in the process itself. Said particles may comprise dust entrained in circulating drying air or it may be dust or fine particles provided by the crushing of the agglomerated microcrystalline mass. In the absence of microcrystalline xylitol, the solid feed of the process may at start-up comprise milled crystalline xylitol from another source. This solid feed should, however, be progressively replaced by microcrystalline xylitol in order to provide a totally microcrystalline structure to the product.

The terms "microcrystalline" and "microcrystal" as used throughout the present specification and claims should be understood to mean very small crystals having a size which on an average is below 50µ, and generally is of the order of about 10µ, on an average. In contrast to the present microcrystals, the xylitol crystals obtainable by prior known crystallization techniques are discrete crystals the particle size of which, on an average, is of the order of about 100–1000µ or larger.

Consequently, the present invention provides a novel particulate crystalline xylitol product wherein each particle substantially throughout its entire structure consists of a multitude of microcrystals of xylitol agglomerated together in a random manner.

Although the size of the xylitol particles according to the present invention is not critical and may vary according to the intended use of the product, the mean particle size of the xylitol product is generally between about 0.1 and 1.0 mm. The preferred mean particle size is generally about 0.15–0.4 mm. The particle size and distribution may be controlled to suit the intended use.

The microcrystals may be used as such from the process, they may be broken up or they may even be cast in the form of ordinary sugar lumps or cubes.

The individual xylitol microcrystals generally comprise anhydrous xylitol. The crystal mass may also include minor portions of amorphous xylitol. In a preferred embodiment of the invention, the microcrystals consist essentially of anhydrous xylitol.

The microcrystalline xylitol product according to the present invention may be used as a bulk sweetener for the total or partial replacement of sucrose or other sweetening agents. Thus, it is useful in dietetic products, in confectionery, bakery products, cereals, desserts, jams, beverages, especially in chocolate, granulated or tabletted table top sweeteners, chewing gums and ice creams, etc. It is also useful in pharmaceuticals where it may comprise the active ingredient or may be included as sweetener, an excipient, a diluent and/or a carrier. The present microcrystalline xylitol may also be used in the production of personal care products and oral hygiene products such as tooth pastes, mouth rinses, etc. The microcrystalline xylitol product according to the present invention can be tabletted into a hard tablet.

A further embodiment of the present invention, relates to a special sweetener which comprises microcrystalline xylitol. Such a sweetener may include other components such as excipients and/or other sweeteners.

Such other sweeteners are preferably also non-cariogenic sweeteners such as intense sweeteners taken from the group comprising dipeptide sweeteners, saccharin, acesulfame K, stevioside, cyclamate, sucralose and neohesperidin dihydrochalcone. However, the preferred non-cariogenic sweetener consists essentially of the microcrystalline xylitol according to the invention.

The other components which may be used in the sweetener and/or other applications such as in pharmaceutical preparations may comprise, for instance, microcrystalline cellulose, carboxymethyl cellulose, polydextrose, dextrose, maltodextrin, lactose, sugar, etc. as well as other sugar alcohols.

The microcrystalline xylitol of the present invention is preferably produced in a pure xylitol form, i.e. containing throughout essentially only xylitol. Thus, the present solid xylitol product can be produced totally without separate binder, which is contrary to the product granulated according to U.S. Pat. No. 5,204,115 with a binder.

The present microcrystalline xylitol may, however, also be microcrystallized with other compounds. Thus, if the solid and/or liquid feed comprises other components, such as one or more of the above mentioned excipients, or other active ingredients, the product discharged from the microcrystallization apparatus will contain said other component (s). A secondary spray of another solid or liquid component may also be fed into the nicrocrystallization apparatus into contact with the microcrystallizing xylitol.

Only such additional components can be used which do not significantly and adversely interfere with the microcrystallization according to the present invention. Specifically, it is necessary that the additional components and the amounts thereof are selected so that the microcrystallizing particles will be substantially dry by the time they leave the suspended state. If the initially dried particles contain too much moisture, they will be clogged together forming large compact structures, wherein the microcrystallization throughout the product cannot be ensured.

Further embodiments of the present invention relate to products made from the novel microcrystalline xylitol. Such products are typically edible products, pharmaceutical products and/or oral hygiene products such as those mentioned above. The microcrystalline xylitol of the present invention may, for instance, be advantageously used in the production of chewing gum. It also provides improvements in tabletting compared to conventional crystalline xylitol.

The present invention will now be described in greater detail. This description should, however, not be taken as limiting the invention to the precise wording thereof. A person skilled in the art will be able to provide numerous modifications and variations of the process without deviating from the invention as defined in the appended claims.

The microcrystalline xylitol produced according to the present invention is shown in the accompanying drawing, wherein.

In the process according to the present invention a liquid containing dissolved xylitol is provided. The solvent component of said liquid is preferably water, although xylitol may also be microcrystallized from other solvents such as alcohols, e.g. ethanol or isopropanol.

The xylitol concentration of said aqueous solution should be between about 30% by weight and about 80% by weight in order to provide a suitable supersaturation at the crystallization. Said concentration is preferably about 50–75% by weight.

Prior to feeding the liquid into a microcrystallization apparatus, the liquid is preferably heated in order to facilitate the subsequent removal of the solvent component and in order to more quickly provide suitable crystallization conditions in said apparatus. An aqueous solution is preferably heated to a temperature of about 45–80° C., preferably about 55–70° C. prior to feeding into said apparatus.

Especially in cases where the solution has a fairly low concentration the temperature should be kept in the lower range in order to avoid dissolving the solid fine particles of xylitol.

The liquid should preferably be distributed in the form of small droplets in the micro-crystallization apparatus. To this end, the liquid is preferably fed at a pressure through a nozzle into said apparatus. In the apparatus the liquid is brought into contact with solid particles containing microcrystalline xylitol which are simultaneously fed into the apparatus so as to be fluidized or suspended in said apparatus.

The solid xylitol particles should comprise microcrystalline xylitol particles. These may be provided by recirculation from the microcrystallization apparatus. Most preferably a fine fraction of the product is recirculated. Such a fine fraction typically has a mean particle size below about 0.2 mm, preferably below about 0.1 mm. However, when larger individual product particles are desired, correspondingly larger xylitol particles may be recirculated or fed into the apparatus from another source. The solid particles may also be dust or fine particles entrained in the drying air and fed back into the apparatus as solid feed.

The liquid is generally contacted with the suspended solid particles in an upper portion of the microcrystallization apparatus. Here the wetted particles and any free droplets of xylitol solution meet a drying gas such as heated air which is introduced into the apparatus to provide removal of the solvent component of said liquid. The drying air is preferably heated to a temperature of about 55–170° C., preferably about 80–150° C., most preferably to about 90–130° C.

The drying should be accomplished in such a way as to substantially remove the solvent while said xylitol material is still in a suspended state. When the solvent is water, said drying should provide a suspended xylitol material dried to a free moisture content of about 0.1 to 3%, preferably below 1%. The free moisture is calculated as any water which is not bound as crystal water in the microcrystallizing xylitol.

In case the drying is not sufficient or too much liquid has been fed into the apparatus, the xylitol material will be too wet and the crystals will stick together to form a dense or syrup-like structure where separate microcrystals can no longer be properly discerned.

A substantial amount of solid xylitol feed is required in order to obtain a satisfactory particulate microcrystalline product. The suitable ratio of liquid xylitol feed to solid xylitol feed varies with the microcrystallization conditions. The ratio should be selected so as to provide a wetting of the solid particle surfaces without dissolving the core of the seed particles. The amount of liquid component also depends on the ease of volatilization of the solvent and on the temperature of the liquid feed as well as the temperature and amount of the drying gas.

The suspended wetted particles may be dried by a co-current or a counter-current stream of drying air. The co-current air will flow downwards with the falling particles while a counter-current air stream will retain the particles in a suspended state for a longer time.

The particles carried downwards with a co-current air stream in a microcrystallization apparatus should be substantially dry by the time they reach the bottom portion of the apparatus and are allowed to settle there. The settling surface is preferably a means allowing building up of a suitable layer and for adjusting the reaction time in the layer. A belt moving at a speed sufficient to allow build up of a porous agglomerated layer of xylitol is generally suitable. The layer typically has a thickness of about 0.5 to 5 cm, preferably about 1–3 cm. The layer should preferably be so porous that air easily penetrates therethrough.

The agglomerated layer of solidified xylitol should further be conditioned so as to allow microcrystallization to proceed in the layer. Said conditioning preferably includes two or more separate steps or phases with different temperatures. The layer is preferably treated e.g. by blowing a hot drying gas therethrough. The temperature and amount of the drying gas is selected so as to provide suitable microcrystallization conditions in the layer. The temperature of the drying gas is typically about 40–150° C., preferably about 50–90° C.

The conditioning may preferably be performed in several successive steps with, for instance, decreasing temperatures of the drying gas so as the ensure a proper drying and microcrystallization of the xylitol.

The conditioning should continue for a sufficient time to allow microcrystallization of any liquid xylitol to take place in the layer. Typically, the conditioning should continue for a time of about 10–180 min or more, preferably about 20–40 min.

After conditioning, the agglomerated particle layer is preferably post-conditioned and cooled or is allowed to cool to ambient temperature. When microcrystalline xylitol is recirculated within the process, care should be taken to recirculate only essentially dry particles. Problems may occur if the dry feed comprises recycled material which is moist and hot. The microcrystallized layer should thus be cooled before milling.

If the surface on which the layer is allowed to settle is flat, the result will be a substantially flat porous and brittle plate comprising microcrystalline xylitol. However, the microcrystallizing xylitol may also be gathered in moulds having any desired form such as resembling ordinary sugar lumps, or bars, strings, cubes, spades, hearts, flowers, etc.

When the microcrystalline product is in the form of a continuous layer, it is generally desirable to break up the agglomerated layer to provide discrete particles. Only a mild comminuting action is required for breaking up the bonds between individual micro-crystals.

The resulting microcrystalline xylitol particles are preferably fractionated after an eventual milling and a portion thereof is recirculated to provide a feed of solid particles containing microcrystalline xylitol into the microcrystallization apparatus.

Generally the microcrystalline xylitol particles are broken up so as to provide particles having a mean particle size of about 0.1–10 mm, preferably about 0.15–0.4 mm. It is generally desirable to recirculate fine particles having a mean particle size below about 0.2 mm, preferably below about 0.1 mm, although larger particles may be recirculated, especially in cases where the desired end product comprises larger particles.

In the case where the drying air is blown countercurrently to the downward movement of the wetted particles in the microcrystallization apparatus, the particles will be fluidized therein. By a suitable fluidization action the particles will be made to recirculate within the apparatus. In the apparatus a simultaneous wetting, drying and microcrystallization of particles will take place. Each particle will pass through several wetting and drying/micro-crystallization stages, colliding with other particles and growing ever bigger until the particle reaches the size and weight wherein the fluidizing air no longer manages to retain them in a fluidized state. At this stage the particles will fall to the bottom of the apparatus and may be removed therefrom to be conditioned, for instance as described above.

The solid feed to the microcrystallization apparatus in the counter-current case preferably comprises dust and fine particles recovered from the circulation of drying air.

In the particulate microcrystalline xylitol product according to the present invention each particle substantially throughout its entire structure consists of a multitude of microcrystals of xylitol agglomerated together in a random manner, The xylitol purity of the product is preferably more than 80%, preferably more than 90%, most preferably up to 98% or more.

In the preferred process about 10–90%, preferably about 30–70% of the dry substance derives from a feed of solid microcrystalline particles, preferably recirculated from the production line or from the drying air. A substantial amount of solid feed is essential in xylitol microcrystallization. The co-current system often requires slightly more solid feed than the counter-current system. Thus, for the co-current drying system, the preferred amount of dry substance deriving from the solid particles is 50–80%.

The microcrystals in each product particle of the present invention are individually very small compared to the crystals formed by prior art crystallization processes. Generally, the size of the microcrystals in each particle is on an average below 50$\mu$, preferably about 10$\mu$ on an average.

Although xylitol crystallizes predominantly in the anhydrous crystal form in the process according to the present invention, also some amorphous xylitol may be present. The degree of crystallinity of the product is, however, generally high. According to DSC measurements the degree of crystallinity is generally as high as 90% or more.

The water content of the preferred microcrystalline xylitol product varies according to production parameters in the range of 0.1% to about 1%, preferably about 0.1 to 0.3%.

The melting behaviour of the preferred microcrystalline xylitol according to the present invention shows one single peak at the melting range of standard crystalline xylitol, i.e. at about 94–96° C.

The invention will now be illustrated with the aid of a few examples. These examples should in no way be taken as limiting the invention.

EXAMPLE 2

The procedure of Example 1 was repeated several times under varying test conditions. The solid feed comprised recirculated microcrystalline xylitol. The test conditions are indicated in Table 1.

The water content of the microcrystalline xylitol product was analyzed by the Karl Fischer method and the melting behaviour was measured by differential scanning calorimetry (DSC). The analysis results of the products are shown in Table 1.

TABLE 1

Xylitol microcrystallization conditions

| Drying | Time min | Feed solution Conc. D.S. % | Feed solution Temp ° C. | Feed bar | Drying air temp. ° C. | Temp. under screen ° C. | Temp. above screen ° C. | Feed dry kg | End product kg | DS from soln. % | Water % |
|---|---|---|---|---|---|---|---|---|---|---|---|
| 1 | 1 | 65.6 | 64–65 | 140 | 104 | 62 | 67 | 2.0 | | | |
|   | 2 |      |       | 150 | 107 | 61 | 62 |     | 2.6 | 23 | 0.1 |
| 2 | 1 | 65.6 | 64–65 | 70  | 107 | 74 | 76 | 1.0 | | | |
|   | 2 |      |       | 70  | 103 | 70 | 64 |     | 1.2 | 17 | 0.6 |
| 3 | 0 | 65.6 | 64–65 | 70  | 105 | 72 | 72 | 1.2 | | | |
|   | 1 |      |       | 70  | 102 | 70 | 66 |     | | | |
|   | 2 |      |       | 60  | 101 | 65 | 57 |     | 1.5 | 20 | 0.7 |
| 4 | 1 | 65.6 | 64–65 | 60  | 104 | 67 | 72 | 1.0 | | | |
|   | 2 |      |       | 70  | 104 | 65 | 62 |     | 1.3 | 23 | 0.1 |
| 5 | 1 | 66.2 | 64–65 | 50  | 108 | 71 | 74 | 1.3 | | | |
|   | 2 |      |       | 60  | 106 | 68 | 65 |     | | | |
|   | 3 |      |       | 60  | 104 | 64 | 59 |     | 1.8 | 28 | 1.8 |
| 6 | 1 | 72   | 64–65 | 55  | 107 | 72 | 72 | 0.6 | | | |
|   | 2 |      |       | 55  | 106 | 70 | 64 |     | 0.9 | 32 | 0.6 |
| 7 | 1 | 72   | 64–65 | 60  | 104 | 67 | 73 | 1.0 | | | |
|   | 2 |      |       | 60  | 103 | 65 | 65 |     | | | |
|   | 3 |      |       | 60  | 102 | 63 | 59 |     | 1.6 | 38 | 0.9 |
| 8 | 1 | 72   | 64–65 | 70  | 107 | 68 | 82 | 1.0 | | | |
|   | 2 |      |       | 70  | 107 | 66 | 72 |     | 1.4 | 29 | 0.8 |

EXAMPLE 1

A xylitol solution (concentration 65.6% by weight, purity over 99% on dry substance) was fed into a heated feed tank. The temperature of the solution in the feed tank was kept at 64±2° C. Solution was supplied from the tank to a spray nozzle at a rate of 27.4 kg/h. The feed pressure of the solution varied from 140 to 150 bar.

Simultaneously with the solution small particles of dried product were fed to the microcrystallization apparatus at a rate of 60 kg/h. Drying air was also fed into the apparatus to dry the sprayed solution and wetted particles. The temperature of the air was adjusted to about 104–107° C. The partly dried mixture of liquid and dry feed fell co-currently with the air-stream towards a screen having a temperature of 62–67° C.

The apparatus was operated under these conditions for four minutes. During this lime an agglomerated, porous powder layer having a thickness of about 1–2 cm built up on the screen. The xylitol layer was conditioned on the screen for about 60 minutes and the temperature dropped slowly from 62° C. to 45° C. The microcrystallized product was collected from the screen, subjected to a gentle milling and sieved.

The water content of the microcrystalline xylitol product was found to be 0.1%.

Dry feed is essential in xylitol microcrystallization. Problems occurred when the dry feed was a recycled material which was moist and hot. The microcrystallized layer should be cooled before milling.

The degree of crystallinity was measured for run No. 8 by DSC and was measured to be about 98%.

EXAMPLE 3

A continuous fluid bed xylitol microcrystallization is performed in an apparatus having a fluid bed drying chamber, equipped with a spray nozzle system inside in the middle of the chamber. The apparatus comprises a bottom screen with a hole for the discharge of the heaviest particles, and a cyclone to recover light particles.

The chamber is loaded with 1 kg of powdered xylitol to act as seed material for the microcrystallization of xylitol. The powdered xylitol is fluidized with a flow of air (temperature 55–85° C.) through the bottom screen. A xylitol solution (concentration 70%, purity over 99% D.S.) at a temperature of 60° C. is fed into the chamber with a pump, atomized by means of a nozzle and sprayed over the fluidized xylitol powder.

The solution is supplied at a rate of 1 kg/h at a pressure of 1.5 bar to the fluidized xylitol powder. The air flow rate is adjusted to fluidize the xylitol and to evaporate water at a rate sufficient to crystallize the xylitol. A microcrystalline xylitol agglomerate is formed when xylitol crystallizes around the xylitol powder particles. The agglomerates remain in a fluidized state until they fall down when their weight is high enough. Xylitol agglomerates are discharged continuously through the bottom hole.

In the drying chamber the lightest, non-agglomerated xylitol particles are removed from the top of the chamber entrained in the exiting air stream. This fine xylitol material is recovered in a cyclone and fed back to the chamber to act as a continuous seed stream.

The discharged agglomerated product is conditioned at a temperature of 45–50° C. for 30 minutes to balance the microcrystallization.

Steady state conditions are reached when all the powdered xylitol used as a starting seed has been discharged from the process. The product obtained thereafter is a totally microcrystalline product which throughout its entire structure consists of microcrystalline xylitol.

EXAMPLE 4

Chewing Gum

A microcrystalline xylitol product having a water content of about 0.08% and a mean particle size of 0.35 mm was evaluated in a standard stick chewing gum production.

The following ingredients were used:

| Ingredient | % Fresh Basis |
| --- | --- |
| Gum base, Nova Base (Dreyfus) | 25.0 |
| Sorbitol Syrup, Sorbifin LS (Xyrofin) | 7.2 |
| Xylitol (Xyrofin) | 55.0 |
| Mannitol, milled (Cerestar) | 8.0 |
| Glycerine (Henkel) | 2.0 |
| Peppermint Flavour liquid (IFF) | 1.2 |
| Peppermint Flavour powder (IFF) | 1.6 |
| Aspartame micronised (Nutrasweet) | q.s (0.05) |

The xylitol was a) standard crystalline xylitol, 90 μm, produced by Xyrofin, and b) microcrystalline xylitol produced according to the present invention.

The chewing gums were produced by placing half of the xylitol in a Z-blade mixer and mixing in the softened gum base. The ingredients were thoroughly combined before the next ingredient was added. Then the sorbitol liquid was added followed by the remaining xylitol, the mannitol and the powdered flavour.

The glycerine was combined with the liquid flavour and aspartame and added to the mixer. As soon as a homogeneous paste was formed, it was removed from the mixer and dusted with milled mannitol. The paste was laminated to required thickness and cut.

The mass produced with both the standard crystalline xylitol and the microcrystalline xylitol was soft and slightly sticky, but once dusted was easily processed and laminated.

The sticks produced were smooth and initially soft, but they became firmer on cooling.

As can be seen from the above results the microcrystalline xylitol is suitable for replacing the standard grade xylitol used for stick chewing gum.

EXAMPLE 5

Toothpaste

| Ingredients | % W/W |
| --- | --- |
| A  PEG-6 | 3.000 |
| Carboxymethyl Cellulose (Aqualon CMC 7MF) | 0.350 |
| B  Sorbitol, 70% Solution Non-Crystallising | 53.117 |
| Sodium Beazoate | 0.500 |
| Tetrasodium Pyrophosphate | 0.500 |
| Titanium Dioxide | 0.500 |
| Microcrystalline Xylitol | 9.900 |
| C  Deionised Water | 6.800 |
| Sodium Fluoride | 0.243 |
| Sodium Saccharin | 0.200 |
| D  Abrasive Silica (Zeodent 113) | 14.000 |
| Thickening Silica (Zeodent 163) | 6.000 |
| Flavour | 0.890 |
| E  30% Sodium Lauryl Sulphate Solution (Empicol 0045) | 4.000 |

Manufacturing Procedure

The following solutions are prepared prior to commencing manufacture of the main batch: 30% Sodium Lauryl Sulphate Solution. All solutions are prepared using deionised water only.

Mucilage Process

1) The components of A are slurried together in a suitable beaker (PEG & CMC).
2) All of the components of B are weighed into a large mucilage vessel. They are mixed together by hand, and then by using a propellor type mixer of silverson set at a slow speed. Mixing is continued until all solids have dissolved and the mixture is homogeneous.
3) The slurry formed in stage 1 is added to the mixture formed in stage 2 and mixing is performed on a high shear mixer (silverson) at high speed for 10 minutes together with additional manual agitation of the vessel. At regular intervals the mixer is stopped and the vessel is thoroughly scraped down. The final mucilage is allowed to be well gelled.
4) The components of C are added to the mixture formed in stage (3). Mixing is continued for a further 10 minutes at high speed on the silverson.
5) The vessel is covered and the mucilage is left to hydrate for 1 hour.
6) The hydrated mucilage (A/B/C) is added to a planetary vacuum mixer, and the components of D (silica and flavour) are stirred in by hand. Once thoroughly blended together mixing under full vacuum for 10 minutes is performed.
7) The mixer is stopped, the vacuum vessel well scraped down, the mixing is continued for a further 10 minutes.
8) The vacuum vessel is scraped down. The SLS (E) is added to the vacuum vessel and gently stirred in by hand. Mixing under full vacuum is performed for 10 minutes.
11) The vessel is scraped down before mixing for a final 10 minutes under full vacuum.
12) The resulting tooth paste mixture is filled into suitable containers.

EXAMPLE 6

Tablets

A sample of microcrystalline xylitol produced according to the present invention was assessed in tablet production and compared to conventional crystalline xylitol (Xylitol C, Xyrofin Oy).

The material under evaluation was mixed in a laboratory scale Turbula mixer for 2 minutes with 0.5% magnesium stearate as lubricant. The mixed sample was then tabletted on a Manesty 2C single punch press using a 15 mm diameter flat-faced bevelled edge punch.

The compression force was adjusted by altering the drop of the top punch. The compression force is indicated by an arbitrary figure. The higher the number, the greater the compression. These figures can only be used as a comparison for each series of compressions. As soon as the material is changed or any of the machine settings are altered the numbers cannot be compared. The adjustment is such that it cannot be exactly reproduced, therefore, these figures should only be seen as a means of differentiating between samples and indicating either increasing or decreasing compression force.

Tablet hardness was measured using a Key Instruments tablet hardness tester which measures the force required to break the tablet across its diameter. Ten tablets were tested and an average reading recorded.

The thickness of ten tablets was measured using a micrometer gauge. The average of ten tablets is recorded.

Ten tablets were weighed individually and an average recorded.

Tablet friability was measured using a Key Instruments friability tester. Ten tablets were dropped 100 times and the percentage weight loss recorded. Any tablets that are badly chipped are removed prior to weighing.

The results obtained from tabletting microcrystalline xylitol are tabulated in Table 2. Tablets pressed from this material produced compacts with a maximum hardness of only about 40 N. The maximum hardness achieved was over 70 N.

The results obtained from tabletting crystalline xylitol are tabulated in Table 3. This material did not tablet well producing poor compacts with a maximum hardness of about 40 N.

TABLE 2

| Microcrystalline Xylitol Sample | | | | |
|---|---|---|---|---|
| Compression* | 33 | 32.5 | 32 | 31.5 |
| Weight (g) | 1.02 | 1.017 | 1.022 | 1.033 |
| Thickness (mm) | 4.141 | 4.141 | 4.168 | 4.277 |
| Hardness (N) | 63(48) | 62(54) | 70(51) | 62(43) |
| Friability (10 tabs) | 100 | 100 | 90.2 | 100 |

TABLE 3

| Crystalline Xylitol | | | | |
|---|---|---|---|---|
| Compression* | 32 | 31.5 | 31 | 30.5 |
| Weight (g) | 1.013 | 0.995 | 1.001 | 1.009 |
| Thickness (mm) | 4.127 | 4.059 | 4.082 | 4.129 |

TABLE 3-continued

| Crystalline Xylitol | | | | |
|---|---|---|---|---|
| Compression* | 32 | 31.5 | 31 | 30.5 |
| Hardness (N) | 35(31) | 37(32) | 42(34) | 38(37) |
| Friability (10 tabs) | 100 | 100 | 100 | 100 |

Figures shown in brackets in Tables 2 and 3 are those taken from analysis performed during production. All other results are from analysis performed ~24 hours after production.
*Compression forces cannot be compared between samples.

The microcrystalline xylitol sample according to the present invention showed an improvement over standard crystalline xylitol in the tabletting test.

EXAMPLE 7

A batch of microcrystalline xylitol produced in accordance with the procedure described in Example 1 was analyzed as to its physical properties. The following analysis methods were used:

Moisture was measured using coulometric Karl Fischer titration DSC analysis was made at a speed of 10° C./minute Flowability: A 500 g sample was poured to a 500 ml measuring cylinder. The sample was tapped 10 times, levelled and the amount of the sample was weighed.

Particle size distribution: Sieve analysis was used to determine the particle size.

Heat of solution: 40 g of the sample was dissolved in 670 g of distilled water at 25° C. The heat of solution was measured with a calorimeter operating in a constant temperature environment.

SEM photos were taken of the microcrystalline xylitol.

The microcrystalline xylitol was compared to a commercial grade crystalline xylitol.

Both xylitols contained 0.1% of water. The DSC diagram of the both xylitols contained one peak at about 94.5–95.5° C. The microcrystalline xylitol had a better flowability and the bulk density was 351/500 ml. The heats of solution and the dissolving times were substantially the same for both xylitols.

Figure 1:
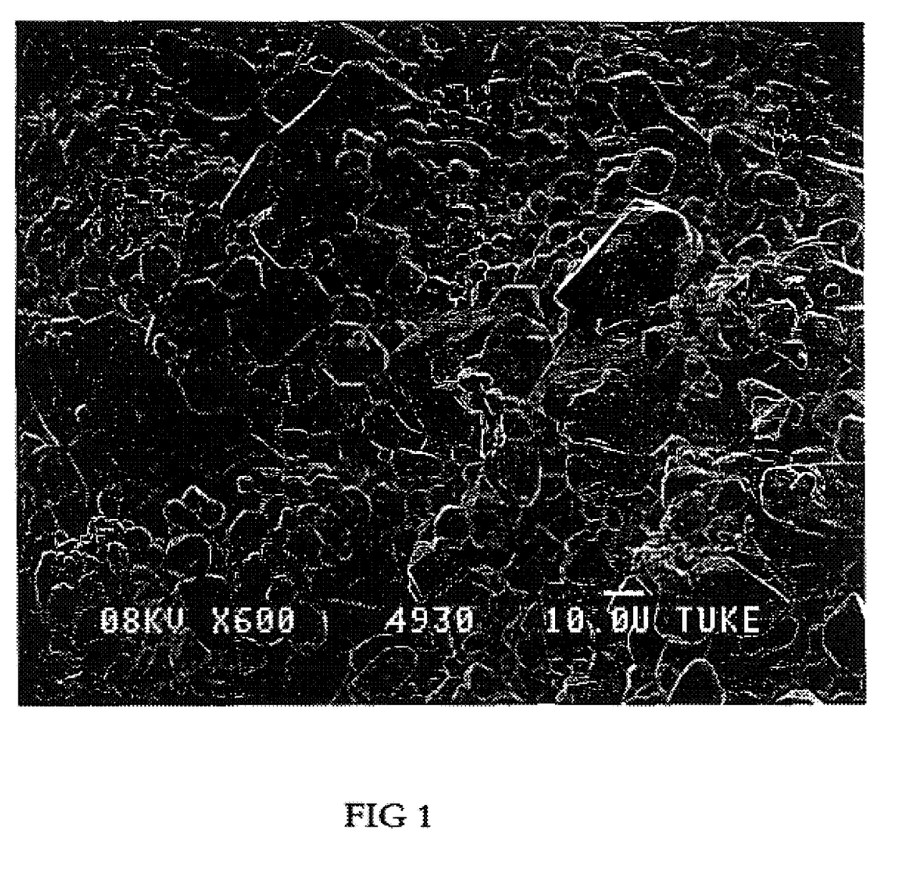
FIG. 1 is a SEM photo showing the microcrystalline xylitol structure in 600× magnification.
Figure 2:
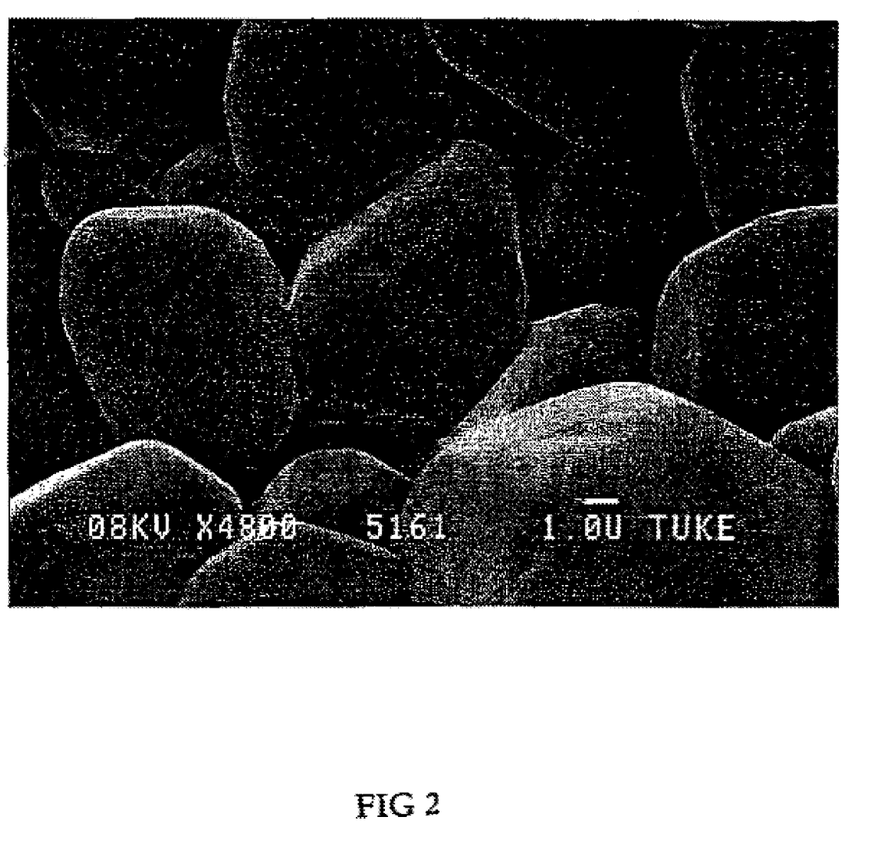
FIG. 2 is a SEM photo showing the microcrystalline structure in 4800× magnification.
Figure 3:
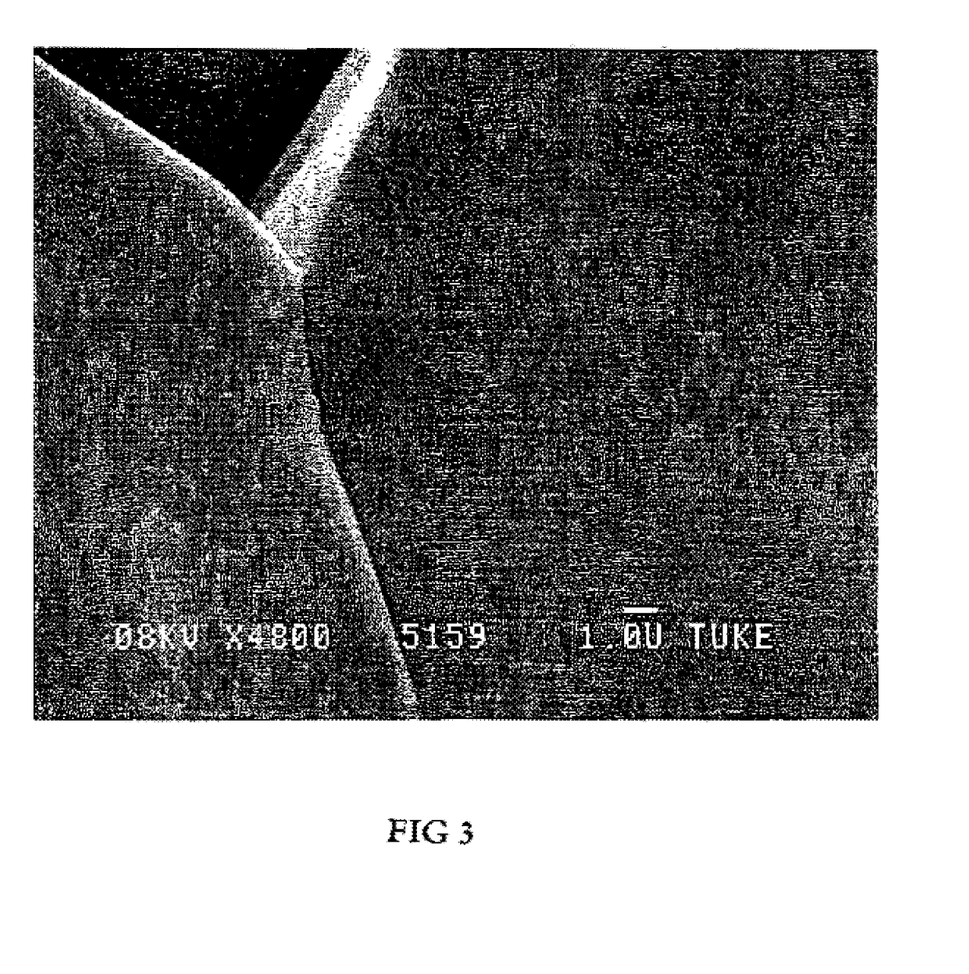
FIG. 3 is a SEM photo showing conventional crystalline xylitol in 4800 magnification.

The microcrystalline xylitol in SEM photos in 600× magnification (FIG. 1) showed a myriad of small crystals looking like normal crystal lumps but smaller. The microcrystalline structure showed very clearly in 4800× magnification (FIG. 2). A comparable SEM photo of conventional crystalline xylitol in 4800×magnification (FIG. 3) indicates the difference in the crystal size.

What is claimed is:

1. A process for the crystallization of xylitol comprising the steps of:
    (a) spraying an aqueous solution of xylitol, said xylitol being present in a concentration of between about 30% and about 80% by weight, into contact with gas suspended fine solid particles containing microcrystalline xylitol;
    (b) causing substantial removal of the water solvent from said aqueous solution in the gas suspended state and allowing the resultant xylitol material to form an essentially solid composition of matter comprising a multitude of microcrystals of xylitol; and
    (c) causing said xylitol composition to be conditioned during a further drying step to provide a product consisting essentially throughout its entire structure of a multitude of microcrystals of xylitol agglomerated together in a random manner.

2. The process according to claim 1 comprising heating said aqueous solution to a temperature of about 45–80° C. prior to said contacting.

3. The process according to claim 1 wherein said aqueous solution contains an excipient, an active ingredient and/or other sweetener than xylitol.

4. The process according to claim 3 wherein a secondary spray of a liquid containing an excipient, an active ingredient and/or other sweetener than xylitol is simultaneously provided.

5. The process according to claim 1 wherein said removal of the water solvent is performed by the introduction of a drying gas heated to a temperature of about 55–170° C.

6. The process according to claim 5 wherein said water solvent removal provides a xylitol material dried to a free moisture content of about 0.1 to 3% while said xylitol material is still in a suspended state.

7. The process according to claim 1 wherein said conditioning is maintained to allow xylitol microcrystallization to proceed in said composition.

8. A process according to claim 1 wherein said xylitol composition is allowed to settle on a moving belt and to form thereon a substantially continuous agglomerated porous powder layer having a thickness of about 0.5–5 cm.

9. The process according to claim 8 wherein said conditioning includes treating said composition in said agglomerated layer with a drying gas having a temperature of about 50–100° C., for a time of about 10–180 minutes.

10. The process according to claim 9, wherein said conditioning is performed in several successive steps with decreasing drying gas temperatures.

11. The process according to claim 9, which further comprises cooling said conditioned agglomerated layer to provide a substantially flat porous and brittle plate comprising microcrystalline xylitol.

12. The process according to claim 10, comprising subjecting said plate to a comminuting action to break up said agglomerated layer.

13. The process according to claim 1 which further comprises fractionating microcrystalline xylitol particles and recirculating at least a portion thereof to provide a feed of said fine solid particles containing microcrystalline xylitol.

14. The process according to claim 13, comprising recovering microcrystalline xylitol particles having a mean particle size of about 0.1–10 mm.

15. The process according to claim 1 wherein about 30–70% of the dried xylitol composition derives from said feed of solid microcrystalline particles.

16. The process according to claim 1 wherein said solid particles are retained in a fluidized state until they have grown to predetermined weight.

17. The process according to claim 1 comprising recirculating microcrystalline xylitol particles having a mean particle size below about 0.2 mm.

18. The process according to claim 1 comprising processing said microcrystalline xylitol optional excipients, carriers and/or active ingredients into a pharmaceutical or oral hygiene product.

19. The process according to claim 1 comprising processing said microcrystalline xylitol into a tablet with optional excipients, carriers and/or active ingredients by direct compression.

20. The processing according to claim 17, comprising processing said microcrystalline xylitol into a chewing gum by mixing with conventional chewing gum ingredients.

21. The process according to claim 1 wherein said aqueous solution of xylitol has a xylitol concentration of 50–77% by weight.

22. The process according to claim 1 comprising heating said aqueous solution to a temperature of about 55–70° C. prior to said contacting.

23. The process according to claim 1 wherein said removal of the water solvent is performed by the introduction of a drying gas heating to a temperature of about 80–150° C.

24. The process according to claim 1 wherein said removal of said solvent is performed by the introduction of a drying gas heated to a temperature of about 90–130° C.

25. The process according to claim 5, wherein said drying gas is air.

26. The process according to claim 5, wherein said solvent removal provides a xylitol material dried to a free moisture content below 1% while said xylitol material is still in a suspended state.

* * * * *